(12) United States Patent
Handelsman et al.

(10) Patent No.: US 6,602,712 B2
(45) Date of Patent: *Aug. 5, 2003

(54) ENTEROTOXIN-DEFICIENT BACILLUS

(75) Inventors: Jo Handelsman, Madison, WI (US); Amy K. Klimowicz, Madison, WI (US)

(73) Assignee: Wisconsin Alumni Research Foundation, Madison, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/287,599

(22) Filed: Apr. 7, 1999

(65) Prior Publication Data

US 2002/0151071 A1 Oct. 17, 2002

Related U.S. Application Data

(60) Provisional application No. 60/080,943, filed on Apr. 7, 1998.

(51) Int. Cl.$^7$ .................. C12N 15/00; C12N 15/75; C12N 15/31; C12N 1/20; C12N 1/21
(52) U.S. Cl. ............... 435/440; 435/471; 435/477; 435/480; 435/252.31; 435/252.5
(58) Field of Search ................. 435/440, 471, 435/477, 480, 252.31, 252.5; 424/93.2, 93.46, 93.461

(56) References Cited

U.S. PATENT DOCUMENTS

| 5,552,138 A | 9/1996 | Handelsman et al. ..... 435/252.5 |
| 5,919,447 A | 7/1999 | Marrone et al. ........ 424/93.461 |

FOREIGN PATENT DOCUMENTS

| WO | WO 95/24126 | 9/1995 |
| WO | PCT/US95/11556 | 3/1996 |

OTHER PUBLICATIONS

Lindback et al. Insertional inactivation of hblC encoding the L2 component of Bacillus cereus ATCC 14579 haemolysin BL strongly reduces enterotoxigenic activity, but not the haemolytic activity against human erythrocytes. Microbiology (England) 1, Nov. 1999.*
Lund et al. Comparison of biological effect of the two different enterotoxin complexes isolated from three different strains of Bacillus cereus. Microbiology (Engalnd) 143(10): p. 3329–36, Oct. 1997.*
Helgason, et al., "*Bacillus anthracis, Bacillus cereus*, and *Bacillus thuringiensis* —One Species on the Basis of genetic Evidence," *Applied and Environmental Microbiology* 66:2627–2630 (2000).
Raffel, et al., "Genotypic and phenotypic analysis of zwittermicin A–producing strains of *Bacillus cereus,*" *Microbiology* 142:3425–343436 (1996).
Stabb, et al., "Zwittermicin A–Producing Strains of *Bacillus cereys* from Diverse Soils," *Applied and Environmental Microbiology* 60:4404–4412 (1994).
Granum et al., Sphingomyelinase is part of the 'enterotoxin complex' produced by *Bacillus cereus, FEMS Microbiology Letters* 110:97–100 (1993).
Heinrichs, et al., Molecular Cloning and Characterization of the *hblA* Gene Encoding the B Component of Hemolysin BL from *Bacillus cereus,* Journal of Bacteriology Nov.:6760–6766 (1993).
Smith et al., "Modeling Dose–Response Relationships in Biological Control: Partitioning Host Responses to the Pathogen andBiocontrol Agent," *Phytopathology* 87:720–729 (1997).

* cited by examiner

*Primary Examiner*—Gabrielle Bugaisky
(74) *Attorney, Agent, or Firm*—Quarles & Brady LLP (57) ABSTRACT

A enterotoxin-deficient mutant of a member strain of the *Bacillus cereus* group does not produce HBL enterotoxin, which has been regarded as a human pathogen found in member strains. An enterotoxin-deficient mutant is suitable for use as a biocontrol agent. Methods for making the mutant and for using the mutant are described.

14 Claims, 4 Drawing Sheets

FIG. 1

*hblA* sequence[*]

```
   1    atg ata aaa aaa atc cct tac aaa tta ctc gct gta tcg acg tta tta act att aca acc
  61    gct aat gta gtt tca cct gta gca act ttt gca agt gaa att gaa caa acg aac aat gga
 121    gat acg gct ctt tct gca aat gaa gcg aag atg aaa gaa act ttg caa aag gct gga tta
 181    ttt gca aaa tct atg aat gcc tat tct tat atg tta att aaa aat cct gat gtg aat ttt
 241    gag gga att act att aat gga tat gta gat tta cct ggt aga atc gta caa gat caa aag
 301    aat gca aga gca cat gct gtt act tgg gat acg aaa gtg aaa aaa cag ctt tta gat aca
 361    ttg act ggt att gtt gaa tat gat acg acg ttt gac aat tat tat gaa aca atg gta gag
 421    gca att aat aca ggg gat gga gaa act tta aaa gaa ggg att aca gat ttg cga ggt gaa
 481    att caa caa aat caa aag tat gca caa caa cta ata gaa gaa tta act aaa tta aga gac
 541    tct att gga cac gat gtt aga gca ttt gga agt aat aaa gag ctc ttg cag tca att tta
 601    aaa aat caa ggt gca gat gtt gat gcc gat caa aag cgt cta gaa gaa gta tta gga tca
 661    gta aac tat tat aaa caa tta gaa tct gat ggg ttt aat gta atg aag ggt gct att ttg
 721    ggt cta cca ata att ggc ggt att ata gtg gga gta gca agg gat aat tta ggt aag tta
 781    gag cct tta tta gca gaa tta cgt cag acc gtg gat tat aaa gta acc tta aat cgt gta
 841    gtt gga gtt gct tac agt aat att aat gaa atc gac aag gcg ctt gat gat gct att aac
 901    gct ctt act tat atg tcc acg cag tgg cat gat tta gat tct caa tat tcg ggc gtt cta
 961    ggg cat att gag aat gca gct caa aaa gcc gat caa aat aaa ttt aaa ttc tta aaa cct
1021    aat tta aat gca gcg aaa gat agt tgg aaa aca tta cga aca gat gct gtt aca tta aaa
1081    gaa gga ata aag gag tta aaa gta gaa act gtt act cca caa aaa tag
```

[*] The underlined segment is deleted from *hblA1*

SEQUENCE LISTING

```
<160> NUMBER OF SEQ ID NOS: 7

<210> SEQ ID NO 1
<211> LENGTH: 1005
<212> TYPE: DNA
<213> ORGANISM: Artificial Sequence
<220> FEATURE:
<223> OTHER INFORMATION: Description of Artificial Sequence: Bacillus
      cereus hblA, having 123 bp in-frame deletion
      spanning nucleotides 568-690
<220> FEATURE:
<221> NAME/KEY: CDS
<222> LOCATION: (1)..(1002)

<400> SEQUENCE: 1 atg ata aaa aaa atc cct tac aaa tta ctc gct gta tcg acg tta tta      48
Met Ile Lys Lys Ile Pro Tyr Lys Leu Leu Ala Val Ser Thr Leu Leu
  1               5                  10                  15 act att aca acc gct aat gta gtt tca cct gta gca act ttt gca agt      96
Thr Ile Thr Thr Ala Asn Val Val Ser Pro Val Ala Thr Phe Ala Ser
             20                  25                  30 gaa att gaa caa acg aac aat gga gat acg gct ctt tct gca aat gaa     144
Glu Ile Glu Gln Thr Asn Asn Gly Asp Thr Ala Leu Ser Ala Asn Glu
         35                  40                  45 gcg aag atg aaa gaa act ttg caa aag gct gga tta ttt gca aaa tct     192
Ala Lys Met Lys Glu Thr Leu Gln Lys Ala Gly Leu Phe Ala Lys Ser
     50                  55                  60 atg aat gcc tat tct tat atg tta att aaa aat cct gat gtg aat ttt     240
Met Asn Ala Tyr Ser Tyr Met Leu Ile Lys Asn Pro Asp Val Asn Phe
 65                  70                  75                  80 gag gga att act att aat gga tat gta gat tta cct ggt aga atc gta     288
Glu Gly Ile Thr Ile Asn Gly Tyr Val Asp Leu Pro Gly Arg Ile Val
                 85                  90                  95 caa gat caa aag aat gca aga gca cat gct gtt act tgg gat acg aaa     336
Gln Asp Gln Lys Asn Ala Arg Ala His Ala Val Thr Trp Asp Thr Lys
            100                 105                 110 gtg aaa aaa cag ctt tta gat aca ttg act ggt att gtt gaa tat gat     384
Val Lys Lys Gln Leu Leu Asp Thr Leu Thr Gly Ile Val Glu Tyr Asp
        115                 120                 125 acg acg ttt gac aat tat tat gaa aca atg gta gag gca att aat aca     432
Thr Thr Phe Asp Asn Tyr Tyr Glu Thr Met Val Glu Ala Ile Asn Thr
    130                 135                 140 ggg gat gga gaa act tta aaa gaa ggg att aca gat ttg cga ggt gaa     480
Gly Asp Gly Glu Thr Leu Lys Glu Gly Ile Thr Asp Leu Arg Gly Glu
145                 150                 155                 160 att caa caa aat caa aag tat gca caa caa cta ata gaa gaa tta act     528
Ile Gln Gln Asn Gln Lys Tyr Ala Gln Gln Leu Ile Glu Glu Leu Thr
                165                 170                 175 aaa tta aga gac tct att gga cac gat gtt aga gca ttt ggg ttt aat     576
Lys Leu Arg Asp Ser Ile Gly His Asp Val Arg Ala Phe Gly Phe Asn
            180                 185                 190 gta atg aag ggt gct att ttg ggt cta cca ata att ggc ggt att ata     624
Val Met Lys Gly Ala Ile Leu Gly Leu Pro Ile Ile Gly Gly Ile Ile
        195                 200                 205 gtg gga gta gca agg gat aat tta ggt aag tta gag cct tta tta gca     672
Val Gly Val Ala Arg Asp Asn Leu Gly Lys Leu Glu Pro Leu Leu Ala
    210                 215                 220
```

```
gaa tta cgt cag acc gtg gat tat aaa gta acc tta aat cgt gta gtt      720
Glu Leu Arg Gln Thr Val Asp Tyr Lys Val Thr Leu Asn Arg Val Val
225                 230                 235                 240 gga gtt gct tac agt aat att aat gaa atc gac aag gcg ctt gat gat      768
Gly Val Ala Tyr Ser Asn Ile Asn Glu Ile Asp Lys Ala Leu Asp Asp
                245                 250                 255 gct att aac gct ctt act tat atg tcc acg cag tgg cat gat tta gat      816
Ala Ile Asn Ala Leu Thr Tyr Met Ser Thr Gln Trp His Asp Leu Asp
            260                 265                 270 tct caa tat tcg ggc gtt cta ggg cat att gag aat gca gct caa aaa      864
Ser Gln Tyr Ser Gly Val Leu Gly His Ile Glu Asn Ala Ala Gln Lys
        275                 280                 285 gcc gat caa aat aaa ttt aaa ttc tta aaa cct aat tta aat gca gcg      912
Ala Asp Gln Asn Lys Phe Lys Phe Leu Lys Pro Asn Leu Asn Ala Ala
    290                 295                 300 aaa gat agt tgg aaa aca tta cga aca gat gct gtt aca tta aaa gaa      960
Lys Asp Ser Trp Lys Thr Leu Arg Thr Asp Ala Val Thr Leu Lys Glu
305                 310                 315                 320 gga ata aag gag tta aaa gta gaa act gtt act cca caa aaa tag         1005
Gly Ile Lys Glu Leu Lys Val Glu Thr Val Thr Pro Gln Lys
                325                 330

<210> SEQ ID NO 2
<211> LENGTH: 334
<212> TYPE: PRT
<213> ORGANISM: Artificial Sequence
<220> FEATURE:
<223> OTHER INFORMATION: Description of Artificial Sequence: Bacillus
      cereus hblA, having 123 bp in-frame deletion
      spanning nucleotides 568-690

<400> SEQUENCE: 2

Met Ile Lys Lys Ile Pro Tyr Lys Leu Leu Ala Val Ser Thr Leu Leu
 1               5                  10                  15

Thr Ile Thr Thr Ala Asn Val Val Ser Pro Val Ala Thr Phe Ala Ser
                20                  25                  30

Glu Ile Glu Gln Thr Asn Asn Gly Asp Thr Ala Leu Ser Ala Asn Glu
            35                  40                  45

Ala Lys Met Lys Glu Thr Leu Gln Lys Ala Gly Leu Phe Ala Lys Ser
        50                  55                  60

Met Asn Ala Tyr Ser Tyr Met Leu Ile Lys Asn Pro Asp Val Asn Phe
 65                 70                  75                  80

Glu Gly Ile Thr Ile Asn Gly Tyr Val Asp Leu Pro Gly Arg Ile Val
                85                  90                  95

Gln Asp Gln Lys Asn Ala Arg Ala His Ala Val Thr Trp Asp Thr Lys
           100                 105                 110

Val Lys Lys Gln Leu Leu Asp Thr Leu Thr Gly Ile Val Glu Tyr Asp
       115                 120                 125

Thr Thr Phe Asp Asn Tyr Tyr Glu Thr Met Val Glu Ala Ile Asn Thr
   130                 135                 140

Gly Asp Gly Glu Thr Leu Lys Glu Gly Ile Thr Asp Leu Arg Gly Glu
145                 150                 155                 160

Ile Gln Gln Asn Gln Lys Tyr Ala Gln Gln Leu Ile Glu Glu Leu Thr
               165                 170                 175

Lys Leu Arg Asp Ser Ile Gly His Asp Val Arg Ala Phe Gly Phe Asn
           180                 185                 190

Val Met Lys Gly Ala Ile Leu Gly Leu Pro Ile Ile Gly Gly Ile Ile
       195                 200                 205
```

```
Val Gly Val Ala Arg Asp Asn Leu Gly Lys Leu Glu Pro Leu Leu Ala
    210                 215                 220

Glu Leu Arg Gln Thr Val Asp Tyr Lys Val Thr Leu Asn Arg Val Val
225                 230                 235                 240

Gly Val Ala Tyr Ser Asn Ile Asn Glu Ile Asp Lys Ala Leu Asp Asp
                245                 250                 255

Ala Ile Asn Ala Leu Thr Tyr Met Ser Thr Gln Trp His Asp Leu Asp
            260                 265                 270

Ser Gln Tyr Ser Gly Val Leu Gly His Ile Glu Asn Ala Ala Gln Lys
        275                 280                 285

Ala Asp Gln Asn Lys Phe Lys Phe Leu Lys Pro Asn Leu Asn Ala Ala
    290                 295                 300

Lys Asp Ser Trp Lys Thr Leu Arg Thr Asp Ala Val Thr Leu Lys Glu
305                 310                 315                 320

Gly Ile Lys Glu Leu Lys Val Glu Thr Val Thr Pro Gln Lys
                325                 330
```

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 3
gaaacaatgg tagaggca                                                18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 4
gcaactccaa ctacacga                                                18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 5
ttactcgctg tatcgacg                                                18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
ccaactatct ttcgctgc                                                18

<210> SEQ ID NO 7
<211> LENGTH: 1128
<212> TYPE: DNA
<213> ORGANISM: Bacillus cereus

<400> SEQUENCE: 7

-continued

```
atgataaaaa aaatcccta caaattactc gctgtatcga cgttattaac tattacaacc        60
gctaatgtag tttcacctgt agcaactttt gcaagtgaaa ttgaacaaac gaacaatgga      120
gatacggctc tttctgcaaa tgaagcgaag atgaaagaaa ctttgcaaaa ggctggatta      180
tttgcaaaat ctatgaatgc ctattcttat atgttaatta aaaatcctga tgtgaatttt      240
gagggaatta ctattaatgg atatgtagat ttacctggta gaatcgtaca agatcaaaag      300
aatgcaagag cacatgctgt tacttgggat acgaaagtga aaaacagct tttagataca       360 ttgactggta ttgttgaata tgatacgacg tttgacaatt attatgaaac aatggtagag      420
gcaattaata caggggatgg agaaacttta aaagaaggga ttacagattt gcgaggtgaa      480
attcaacaaa atcaaaagta tgcacaacaa ctaatagaag aattaactaa attaagagac      540
tctattggac acgatgttag agcatttgga agtaataaag agctcttgca gtcaatttta      600
aaaaatcaag gtgcagatgt tgatgccgat caaaagcgtc tagaagaagt attaggatca      660
gtaaactatt ataaacaatt agaatctgat gggtttaatg taatgaaggg tgctattttg      720
ggtctaccaa taattggcgg tattatagtg ggagtagcaa gggataattt aggtaagtta      780
gagcctttat tagcagaatt acgtcagacc gtggattata aagtaaccttt aaatcgtgta     840 gttggagttg cttacagtaa tattaatgaa atcgacaagg cgcttgatga tgctattaac     900
gctcttactt atatgtccac gcagtggcat gatttagatt ctcaatattc gggcgttcta      960
gggcatattg agaatgcagc tcaaaaagcc gatcaaaata aatttaaatt cttaaaacct    1020
aatttaaatg cagcgaaaga tagttggaaa acattacgaa cagatgctgt tacattaaaa    1080
gaaggaataa aggagttaaa agtagaaact gttactccac aaaaatag                 1128
```

ENTEROTOXIN-DEFICIENT BACILLUS

CROSS-REFERENCE TO RELATED APPLICATIONS

This application claims the benefit of U.S. Provisional Application No. 60/080,943 filed Apr. 7, 1998.

STATEMENT REGARDING FEDERALLY SPONSORED RESEARCH OR DEVELOPMENT

Not applicable.

BACKGROUND OF THE INVENTION

Significant research has been conducted in recent years on the use of biological agents to increase agricultural productivity and efficiency. Biological control based on the use of microorganisms to suppress plant pests offers an attractive alternative to chemical pesticides which are less favored than they have previously been because of concerns about human health and environmental quality. Several screening programs have been used before to isolate biological agents which are effective in the laboratory or in the field to combat pests or facilitate plant growth.

"Biological control" or "biocontrol" is defined as pathogen suppression by the use of a second organism. Mechanisms of biological control are diverse. For example, certain bacteria have been examined for their usefulness in biological control of root rot in alfalfa. It is believed that control is obtained by competition or antagonism between the bacteria and the fungi on the surface of the alfalfa roots. In contrast, a toxin produced by one species of bacteria may be used to control another species of bacteria or other microorganism that appears as a pathogen. Bacterially produced antibiotics are examples of such toxins. The toxin can be isolated from the species producing it and administered directly, as is the common procedure with penicillin, or the species itself may be administered under appropriate circumstances to produce the toxin in situ. Once identified, such toxins produced by soil-dwelling bacteria may have utility in diverse other areas as antifungal or antibiotic agents.

An example of a biological control agent into which significant scientific and economic development has occurred is *Bacillus thuringiensis*. *B. thuringiensis* strains produce toxic proteins which have the ability to specifically kill certain insects. Significant further research has identified a large number of *B. thuringiensis* strains having variations in target range and efficacy. In addition, research has been conducted on methods for stabilizing and applying such toxins, or strains harboring them, to a wide variety of field crop situations. It was also discovered that knowledge of *B. thuringiensis* strains was largely transferable to new strains since the toxins required for biological control and methods for preparing inocula for use in the field were generally similar among strains.

*B. cereus* (Bc) is closely related to *B. thuringiensis* (Bt), which has been used for insect biocontrol for about 30 years. Bc and Bt are generally considered to be members of a single species and the names are artifacts of history (Ash et al., 1991a,b; Carlson et al., 1994; Gordon, 1975; Logan and Berkeley, 1984; Lysenko, 1983; Priest, 1993; and Zahner et al., 1989). The major difference between Bc and Bt appears to be the presence of plasmids in the latter that encode an insecticidal crystal toxin responsible for insect biocontrol by Bt. Bc is a known food contaminant that can cause diarrhea in humans. Outbreaks of Bc food poisoning are associated with improper food storage and handling and require ingestion of large numbers of Bc spores (Gilbert, 1979). There have been no reported outbreaks of food poisoning associated with Bt use, presumably because it does not reach the human food supply in sufficient populations to cause a problem.

Previously it has been found that a specific strain of *Bacillus cereus*, which has been referred to both as UW85 and by its ATCC designation 53522, has biocontrol efficacy in many applications. See, e.g., U.S. Pat. No. 4,877,738. UW85 has proven to be an effective biocontrol agent of damping-off and root-rot diseases of soybeans and alfalfa under diverse field conditions in the upper Midwest U.S. (Handelsman et al., 1990; Osburn et al., 1995). The UW85 *B. cereus* strain protects alfalfa seedlings from damping off caused by *Phytopthora medicaginis* (Pmm), tobacco seedlings from *Phytopthora nicotianae*, cucumber fruits from rot caused by *Pythium aphanidermatum*, and peanuts from *Sclerotinia minor*. In a five-year field study on soybeans, UW85 applied either on the seed or in-furrow increased soybean yields significantly in all five years at a site with high disease pressure; yield enhancements were typically in the range of 35% to 139% depending on the severity of disease. In each year, the magnitude of the yield effect of UW85 was similar to that of Ridomil, the in-furrow formulation of metalaxyl, which controls Oomycete pathogens (Osburn et al., 1995). UW85 has been extensively field-tested and is currently in review by EPA for registration as a seed treatment for various crops.

UW85 produces two antifungal compounds that independently contribute to suppression of damping-off fungi. The more potent of these compounds, is zwittermicin A, a novel aminopolyol (Silo-Suh et al., 1994; He et al., 1994). Other, diverse strains of *B. cereus* found in all tested soils also suppress plant disease and produce zwittermicin A (Stabb et al., 1994; Raffel et al., 1996). Thus, this species has broad potential for biocontrol applications. The second compound is kanosamine, a well known aminoglycoside antibiotic.

Inoculation with *B. cereus* appears to have a negligible long-term impact on the environment. This species is common and present in all soils we have tested at approximately $10^4$ cfu/gm soil (Stabb et al., 1994; Raffel et al., 1996). Data suggest that roots have a carrying capacity for Bc since by the end of the growing season, soybean roots derived from seeds treated with Bc UW85 had the same populations of Bc as untreated roots. However, the treated roots carried UW85 whereas untreated roots carried indigenous Bc strains (Halverson et al., 1993). Therefore, it appears that when UW85 is applied to seeds, it colonizes the roots of the plant at low populations and then dies off to the background level by the end of the season, suggesting that it will have minimal environmental impact. We have shown that early in the season, treatment of seeds with UW85 can result in a change in the microbial community on roots (Gilbert et al., 1993), but this effect does not seem to be sustained beyond the first 10 days (Raffel and Handelsman, unpublished). Overall, the existing data suggest that seed treatment with UW85 is a benign environmental event since Bc is a common soil bacterium and UW85 does not maintain high populations for long, which is in concert with other studies of Bacillus (Kim et al., 1997).

There is significant interest in developing numerous strains of Bc as inoculants for disease suppression on field crops, fruit and vegetable crops, greenhouse and ornamental production, and turf management, and in choosing strains adapted to particular host species or geographic locations. Other such strains have been identified. Thus, the invention disclosed herein will have application to many strains of Bc, not just to UW85 and the other strains noted herein.

Biocontrol has long been thought to be safer for the environment and human health than synthetic pesticides (Cook et al. 1996; Benbrook et al., 1996). As more bacterial biocontrol agents have reached the federal regulatory agencies for review, the relatedness of some of the bacteria and human pathogens has raised concerns by the agencies themselves and the public. For example, a recent registration application for a soil isolate of *Burkholderia cepacia* (Parke et al., 1991) raised concern from the cystic fibrosis community because members of this bacterial species are opportunistic pathogens of cystic fibrosis patients (Govan and Deretic, 1996).

There is some evidence to suggest that the *B. cepacia* biocontrol strains are genetically and physiologically different from the human isolates, but the risks associated with use of these bacteria remain in question. This type of issue is likely to emerge more frequently as biocontrol research yields a greater diversity of strains. Many of the strains being developed for biocontrol are common soil bacteria, and many soil bacteria are, or have close relatives that are, human pathogens. It is therefore essential to assess the environmental exposure associated with use of these organisms and determine whether that exposure is greater with biocontrol practices than with standard agricultural practices. Furthermore, there is an excellent opportunity to use the powerful techniques of genetic engineering to make biocontrol organisms safer by deleting genes associated with unwanted activities. This will have two impacts: providing biocontrol agents that pass regulatory review, and providing the public with examples of genetic engineering used to make the food supply safer.

Despite the good safety record of Bt, lingering concerns remain about registration of products containing Bt or Bc. Many strains of Bc and Bt produce an enterotoxin, denoted HBL, that is associated with mammalian toxicity (Beecher and Macmillan, 1991; Beecher et al., 1995). All of the major Bt strains on the commercial market produce HBL (Damgaard, 1995) and, as a result, the EPA has expressed hesitation about future registration of Bt strains. Bc is a recognized food toxicant and therefore must be demonstrated to be safe before it is used as an inoculant. There is strong evidence that HBL is responsible for the toxicity of most pathogenic Bc strains because purified HBL mimics Bc toxicity and there is a high correlation between toxicity and HBL production among Bc strains. The two key issues with Bc inoculant strains are the presence of the gene for enterotoxin production and any associated potential for human exposure to Bc from food grown from Bc-treated seed. It is not known whether other members of the so-called Bacillus cereus group, namely the *B. anthracis* strains, produce the enterotoxin, although both *B. cereus* and *B. thuringiensis* do produce the enterotoxin.

HBL is a tripartite enterotoxin, that includes a binding component, B, and two lytic components, $L_1$ and $L_2$ (Beecher and Macmillan, 1991). All three components are absolutely necessary for enterotoxigenic activity, as assessed by fluid accumulation in the ligated rabbit ileal loop assay and vascular permeability, which are currently the best animal models for Bc toxicity (Beecher et al., 1995; Glatz et al., 1974).

The genes encoding each of the components have been cloned and sequenced, and appear to be cotranscribed in an operon in the order $L_2$, $L_1$, B (Heinrichs et al., 1993; Ryan et al., 1997). Studies indicate that HBL production is a common trait among strains of *B. cereus* isolated from a variety of sources, including flour, rice, dairy products, and soil (Carlson et al., 1994; Damgaard et al., 1996; Granum et al., 1993; Lee et al., 1995; Mosso et al., 1989; Te Giffel et al., 1997; Yusuf et al., 1992).

A PCR screen of nearly 175 soil and root isolates for hblA using primers derived from the sequence of the hblA gene published by Heinrichs et al., 1993 showed that approximately 70% contain hblA, the gene that encodes the B component (Raffel and Handelsman, unpublished). UW85 contains this gene and produces the toxin when grown in tryptic soy broth as shown by ELISA with antiserum against HBL.

In addition to being the most important and widespread toxin in Bc, HBL is the only known mammalian toxin in strain UW85. In addition to being important biologically, HBL is important from a regulatory perspective. EPA requests data about the production of HBL (and not about other toxins) prior to registration of Bc and Bt strains.

What is lacking in-the art is a strain in the *Bacillus cereus* group having utility as a biocontrol agent that is also deficient in the HBL enterotoxin. The present invention responds to that regulatory concern as well as the scientific evidence that HBL is important in mammalian toxicity by Bc.

BRIEF SUMMARY OF THE INVENTION

The present invention is summarized in that a mutant Bacillus strain is deficient in the enterotoxin HBL. The invention is further summarized in that the mutant strain is obtained by altering at least one of three polynucleotide sequences that otherwise would encode a component of the HBL enterotoxin, so that the polynucleotide sequence can no longer encode a functional component and, therefore, an active HBL enterotoxin cannot be produced.

The present invention is further summarized in that a genetic construct for use in accordance with the present invention contains an allele of a polynucleotide sequence that encodes at least one inactive component of HBL enterotoxin.

It is an advantage of the present invention that the enterotoxin can be eliminated from the Bacillus without adding any new DNA in the organism. Therefore, under the current EPA definition of genetic engineering (Federal Register 1997, 17910–17958), the resulting mutants are not considered genetically engineered and will not be subject to any regulations that do not apply to the wild type strain.

Other objects, advantages and features of the invention will become apparent upon consideration of the following detailed description taken in conjunction with the accompanying drawings.

BRIEF DESCRIPTION OF THE SEVERAL VIEWS OF THE DRAWINGS

FIG. 2 depicts the coding sequence of hblA SEQ ID NO:7. The underlining represents the portion of hblA that is deleted in the preferred embodiment of the present invention.

DETAILED DESCRIPTION OF THE INVENTION

In a first aspect, the present invention is a mutant member of the *Bacillus cereus* group that is deficient in HBL enterotoxin. An enterotoxin-deficient mutant of the present invention does not produce an active HBL enterotoxin, although it may produce fewer than all three components of wild-type HBL enterotoxin. However, since all three distinct components of the enterotoxin are required to produce an active toxin, a mutant of the present invention can encompass a mutation in any one or more of the polynucleotides that encode the components.

The mutation in any of the polynucleotides can be a point mutation, a deletion, an insertion or a rearrangement that is sufficient to render the component ineffective in combination with the remaining components to form active HBL enterotoxin. Although the applicants have exemplified below a defined deletion mutant of the hblA gene, the invention can readily be practiced using a different deletion, or another type of mutation in hblA, or with a comparable mutation in hblC or hblD. The mutant strain can alternatively include a change in a sequence that encodes a protein or peptide that acts in trans to modify one or more of the HBL components. In addition to any change that inactivates a component, the polynucleotide encoding the component can also include additional changes that may not otherwise alter the function of the component. Such mutants would fall within the scope of the invention as long as they are unable to produce HBL enterotoxin by virtue of a change in at least one polynucleotide that encodes a component of the enterotoxin. Isolated preparations of naturally occurring mutants can also fall within the scope of the present invention.

The enterotoxin-deficient mutants of the present invention can be mutants of any member of the *Bacillus cereus* group of bacteria, including *B. cereus, B. thuringiensis* and *B. anthracis*. Preferably, the mutant is also characterized by having a biological control activity when used as an active agent in an inoculum, as described infra.

In a second aspect, the invention is a method for producing a enterotoxin-deficient mutant of the present invention, wherein the method comprises the step of modifying in a Bacillus strain at least one polynucleotide that encodes a component of the HBL enterotoxin. The component can be modified by altering the polynucleotide that encodes the component, for example, by gene replacement. A suitable method for gene replacement, described in the accompanying Examples, employs a vector carrying a desired mutation that alters the HBL enterotoxin component. The vector can be cured from cells at a non-permissive temperature, and further permits selection of mutants on the basis of resistance or sensitivity to an antibiotic.

The invention has particular utility when applied in strains of *Bacillus cereus* that produce biocontrol antibiotics such as zwittermicin A. Such strains include, but are not limited to, *Bacillus cereus* strains UW85 (ATCC 53522), A54-12 (ATCC 55609), MS 1-9(ATCC 55812), and DGA34 (ATCC 55608). These strains are disclosed in U.S. Pat. Nos. 4,877,738; 5,552,138; 5,700,462; and 5,736,382 (which issued on Apr. 7, 1998), respectively, all of which are incorporated herein by reference in their entirety. One or more mutations that inactivate at least one component of the three components that comprise the HBL enterotoxin can be introduced into a zwittermicin-producing strain, thereby eliminating the enterotoxin from the strain and obviating safety concerns about the human pathogenicity of the modified strain. Since *B. thuringiensis* is very closely related to *B. cereus*, and contains the HBL enterotoxin, it is further specifically envisioned that a mutation of the type disclosed herein can be introduced into *B. thuringiensis* in the same manner as is described herein.

In a further aspect, the invention is a method for biological control of plant pathogens, where the method comprises applying an inoculum that includes as an active agent a novel enterotoxin-deficient mutant of a strain in the *Bacillus cereus* group. The active agent is preferably an enterotoxin-deficient *B. cereus* strain. The mutants of the present invention can be used in a method for biological control in the same ways as UW85 and other such mutants, the methods for use being fully described, for example, in U.S. Pat. No. 4,877,738, previously incorporated herein by reference in its entirety. A suitable assay for monitoring the biocontrol activity of an enterotoxin-deficient strain of the present invention is a tomato emergence biocontrol assay as described by Smith, K. P., Handelsman, J., and Goodman, R. M., Modeling dose-response relationships in biological control: Partitioning host responses to the pathogen and biocontrol agent, *Phytopathology* 87:720–729 (1997), incorporated herein by reference in its entirety.

The invention will be better understood upon consideration of the following examples which are considered to be exemplary and non-limiting on the scope of the invention.

EXAMPLES

Materials and Methods

Bacterial strains, plasmids, and media. *E. coli* DH5α was used for cloning. *Bacillus thuringiensis* strain EG10368 (Deposited under accession number NRRL-B-21125 in the permanent collection of the Agricultural Research Service Culture Collection, Northern Regional Research Laboratory, U.S. Dept. of Agriculture, 1815 N. University Street, Peoria Ill. 61604, see U.S. Pat. No. 5,204,237) was obtained from Ecogen Inc., Langhorne, Pa. *Bacillus cereus* strain AS4–12 (Deposited under accession number 55609 with the American Type Culture Collection, now located at 10801 University Boulevard, Manassas, Va. 20110–2209) was isolated from soil from an alfalfa field in Arlington, Wis. (Stabb et al., 1994) and is described in published International Patent Application No. PCT/US96/09496, incorporated herein by reference in its entirety. *E. coli* was grown in Luria-Bertani liquid or solid media. *B. cereus* and *B. thuringiensis* were grown in 50% tryptic soy broth (TSB) or on 50% tryptic soy agar (TSA) plates (Difco Laboratories, Detroit, Mich.). Antibiotics were used at the following concentrations: for *E. coli*, ampicillin at 100 µg/ml; for *B. cereus* and *B. thuringiensis*, chloramphenicol at 5 µg/ml.

The hblA gene cloned from *B. cereus* F837/76 was provided by Amy Wong at the Food Research Institute in Madison, Wis. It was previously cloned on a 2.1-kb EcoR1 fragment into pUC18 (Heinrichs et al., 1993, incorporated herein by reference in its entirety, sequence available in GenBank at accession number L20441).

DNA isolation and manipulation. Plasmid DNA was isolated from *E. coli* using Qiagen plasmid prep kits (Qiagen Inc., Chatsworth, Calif.). Plasmid DNA was isolated from *B. cereus* and *B. thuringiensis* by the alkaline lysis method described by Bron, S., "Plasmids" in Hardwood, C. R. and S. M. Cutting (eds.), *Molecular Biological Methods for Bacillus*, p. 75–174, John Wiley and Sons, Ltd., N.Y. (1990), incorporated herein by reference in its entirety, except Solution A was supplemented with 8 µg/ml of RNase A.

Ligation reactions were performed by standard methods (Sambrook et al., 1989). When necessary, DNA restriction fragments were purified from agarose gels using the QIAEX II Gel Extraction Kit (Qiagen Inc., Chatsworth, Calif.).

Figure 1:
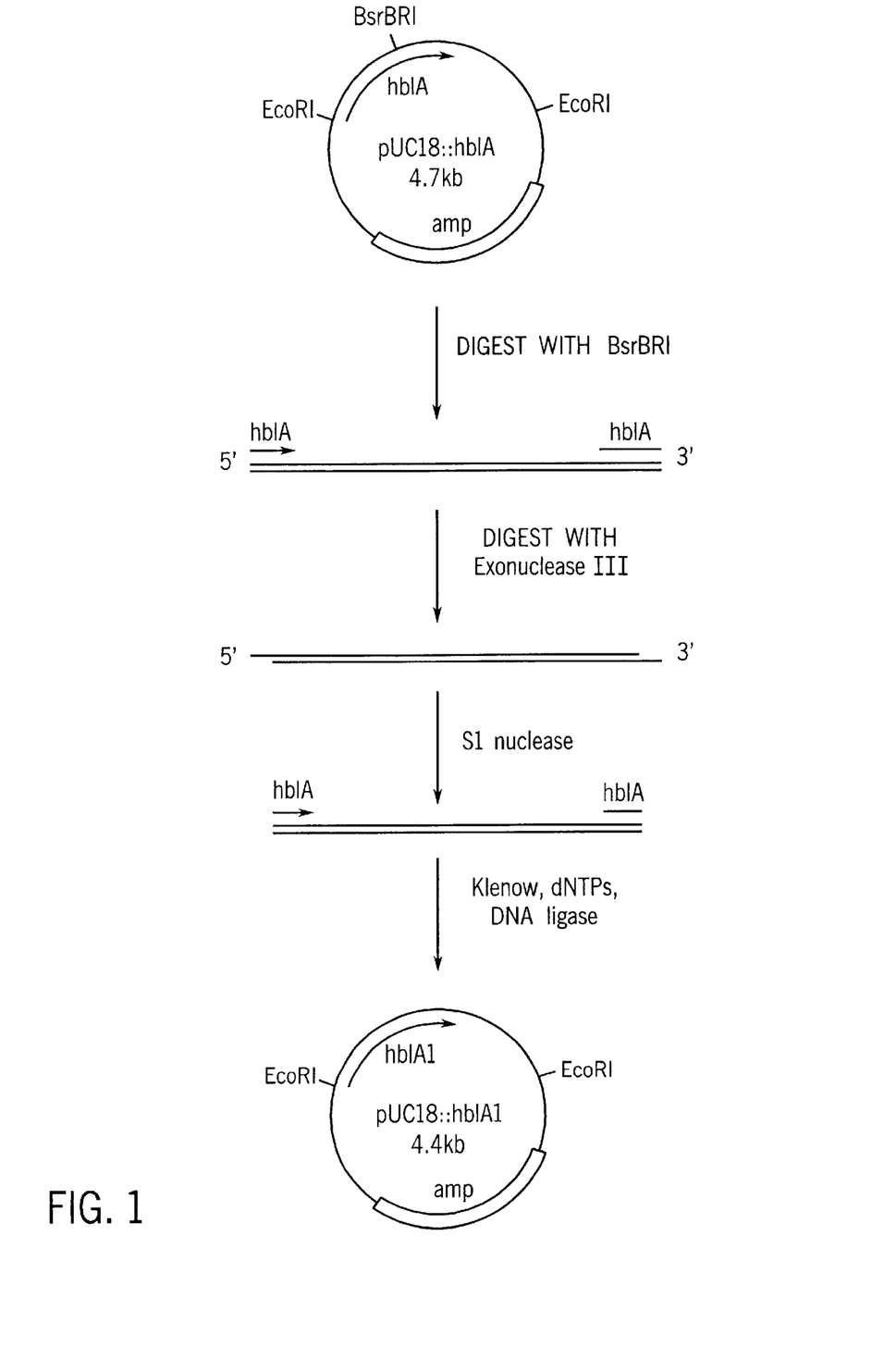
FIG. 1 depicts the construction of vector (pUC18::hblA1) that contains an hblA deletion allele, denoted hblA1, in accordance with the present invention.
Figure 3:
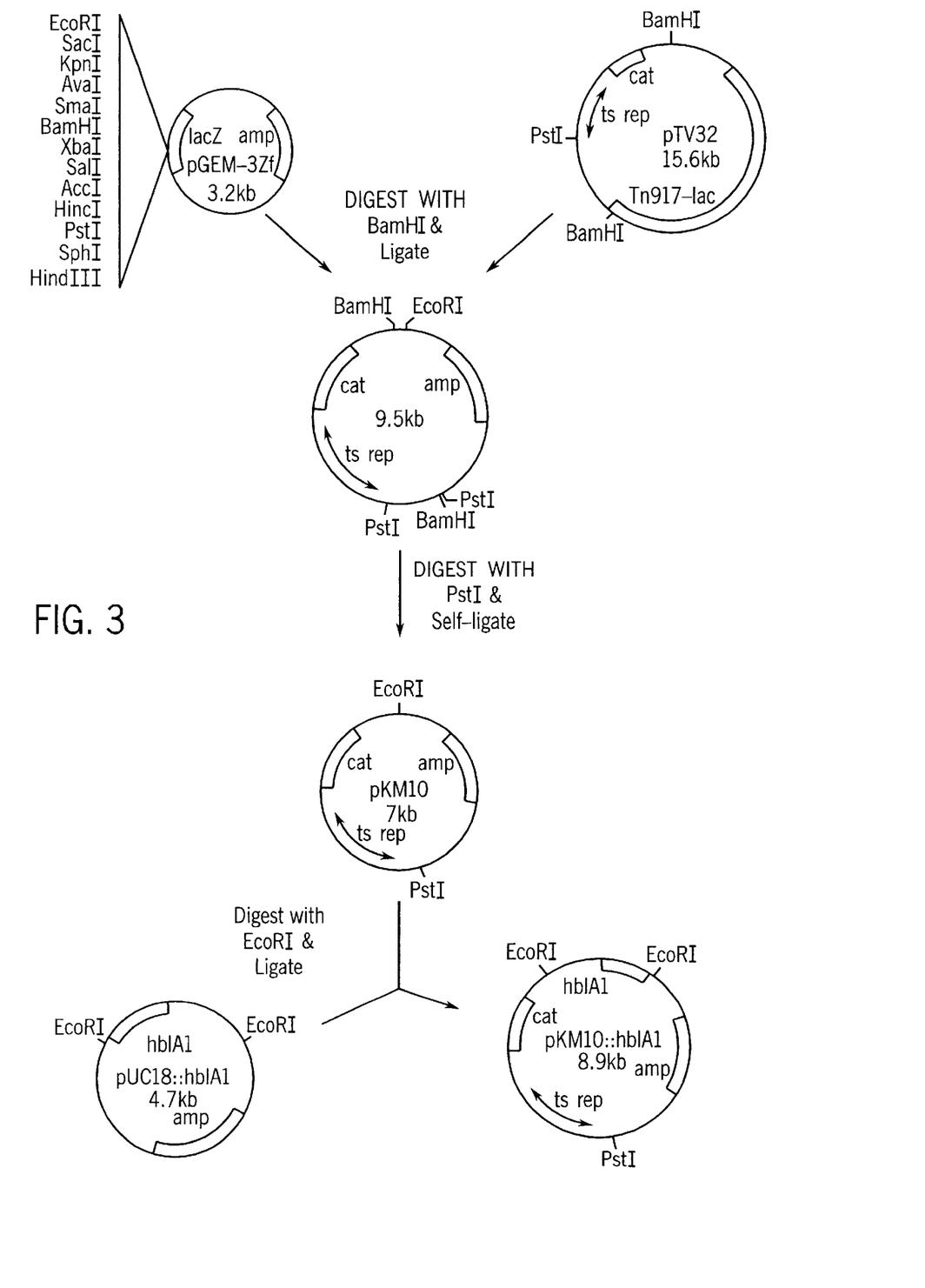
FIG. 3 depicts the construction of a vector (pKM10::hblA1) containing an hblA deletion allele in accordance with the present invention.
Figure 4:
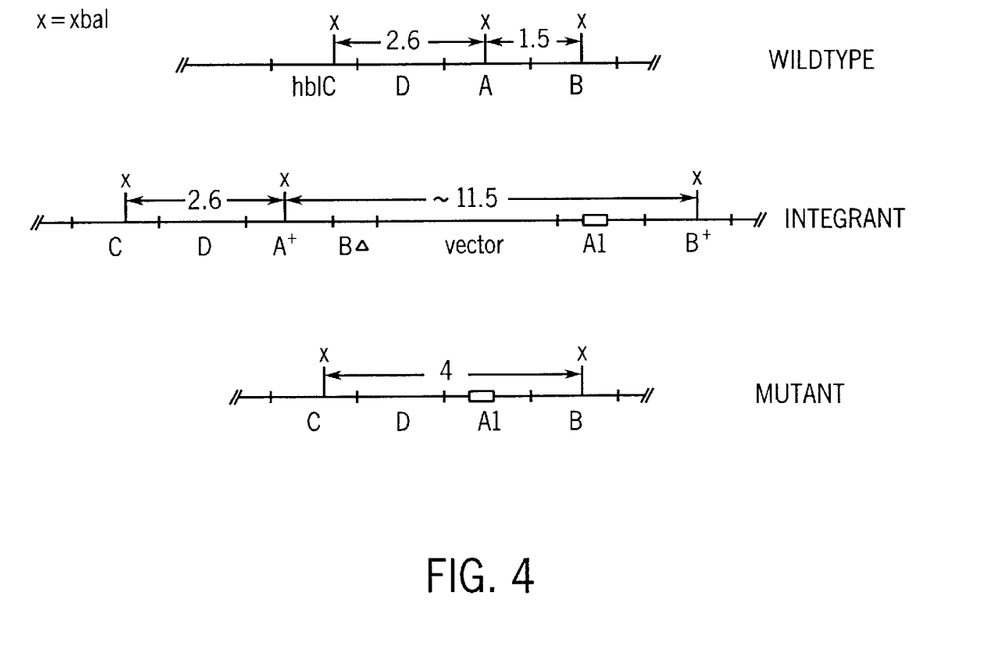
FIG. 4 depicts the wild type hbl operon of a Bacillus chromosome (top), a vector comprising the hblA1 mutation integrated into the Bacillus chromosome after a single recombination event (center), and the hblA1 mutation integrated into the Bacillus chromosome after a second recombination event that excises the vector sequences from the chromosome (bottom).

Internal deletions in hblA were constructed with the Erase-a-Base deletion generation system (Promega Corp., Madison, Wis.). pUC18::hblA was cleaved with BsrBRI, a unique restriction site near the center of hblA, a portion was removed by exonuclease III digestion, and the plasmid was religated (FIG. 1). The mutant allele, designated hblA1 (presented in SEQ ID NO:1), was sequenced across the deletion with the ABI PRISM Dye Terminator Cycle Sequencing Ready Reaction Kit (Perkin-Elmer Corp., Foster City, Calif.), and the sequencing gel was run by the University of Wis. Biotechnology Center. Both strands of hblA1 were sequenced, using the following primers which are based on the published sequence of hblA (Genbank accession number L20441): hblA1-F, 5'-GAAACAATGGTAGAGGCA-3' (SEQ ID NO:3); hblA1-R, 5'-GCAACTCCAACTACACGA-3' (SEQ ID NO:4). Mutant allele hblA1 is characterized as having a 123 bp in-frame deletion spanning nucleotides 568–690 of the coding region identified by Heinrichs, supra. The amino acid sequence of the component encoded by hblA1 is depicted at SEQ ID NO:2.

Transformations. Competent cells of E. coli (50 μl) were electroporated in 0.2-cm cuvettes with a Gene Pulser apparatus (Bio-Rad, Richmond, Calif.) set at 25 μF, 200Ω and 1.8 kV. Cells were transferred to 2 ml of LB and allowed to recover for 1 hr at 37° C. with shaking before plating on selective media.

Preparation of competent cells and electroporation of B. cereus and B. thuringiensis were performed as described previously (Silo-Suh et al., 1994), except the transformed cells were incubated for 2 hours at 28° C. before plating. B. cereus apparently restricts methylated DNA from E. coli (Blackson and Handelsman, unpublished data), as was reported for *Bacillus thuringiensis* (Macaluso, A. and Mettus, A.-M., 1991). Therefore, recombinant plasmids isolated from *E. coli* were passed through *B. thuringiensis* EG10368, a highly transformable strain, before being introduced into *B. cereus* AS4–12 by electroporation.

Southern hybridization analysis. Total genomic DNA from *B. cereus* was obtained using the Easy-DNA Kit (Invitrogen Corp., Carlsbad, Calif.). To enhance cell lysis, the resuspended cells were vortexed for 4 min. with 50–75 $\mu$l of 0.1 mm zirconia/silica beads. Probe labeling and Southern hybridization analysis of *B. cereus* genomic DNA were performed as described previously (Milner et al., 1996). Genomic DNA was digested with XbaI and electrophoresed on a 0.8% agarose gel. Blots were probed with either pKM10 or a fragment of hblA. For the hblA probe, a 1022-bp internal fragment of the coding region was amplified by PCR using the following primer set: hblA-F, 5'-TTACTCGCTGTATCGACG-3' (SEQ ID NO:5); hblA-R, 5'-CCAACTATCTTTCGCTGC-3' (SEQ ID NO:6).

Western immunoblot analysis. Culture supernatant for Western blot analysis was prepared essentially as described previously (Beecher and Wong, 1994). Stationary cultures of the strains were grown in BHIG at room temperature overnight. Flasks (250 ml) containing 50 ml of BHIG were inoculated with 0.5% (vol/vol) of the overnight cultures and grown on a rotary shaker (200 rpm) for 5–6 hr at 30° C. to 320° C. EDTA was added to each culture to a final concentration of 10 mM. The cultures were centrifuged at 4° C. for 15 min at 14,600×g and the culture supernatants were filter sterilized with 0.22-$\mu$m pore-sized filters and, if necessary, concentrated by ultrafiltration (Centricon-10 concentrators, Amicon, Inc., Beverly, Mass.; Ultrafree-4 centrifugal filtration devices, Millipore Corp., Bedford, Mass.). The supernatants were stored at −20° C. Sodium dodecyl sulfate-polyacrylamide gel electrophoresis (SDS-PAGE) was performed by standard methods (Laemmli, 1970). Proteins were transferred to a polyvinylidine defluoride (PVDF) membrane in a Trans-Blot electrophoretic transfer cell (Bio-Rad) overnight at 35 V and 4° C. Blotted proteins were probed with either preimmune rabbit serum or polyclonal antiserum prepared against purified B component from *B. cereus* F837/76 as described previously (Beecher et al., 1995). Immune complexes were detected with horseradish peroxidase-labeled goat anti-rabbit antibodies (Sigma), and visualized by chemiluminescence following treatment with ECL kit reagents (Amersham Life Sciences, Buckinghamshire, England). The molecular weights of the proteins are only approximate because they were referenced to prestained protein standards, whose apparent molecular weights can vary significantly relative to unstained protein standards.

PCR analysis. Genomic DNA for PCR analysis was prepared by the rapid cell-lysis method as described previously (Raffel et al., 1996), or with the Easy-DNA Kit. PCR reactions were performed with the hblA-F/hblA-R primer set in a thermocycler (RoboCycler 40, Stratagene, La Jolla, Calif.) with the following program: 40 cycles of 1 min at 94° C., 1 min at 56° C., and 2 min at 72° C.; and a final 5 min extension at 72° C.

Construction of a Ts plasmid for gene replacement. A temperature-sensitive (Ts) shuttle vector, pKM10, capable of replication in *B. cereus* and *E. coli* was constructed for performing the gene replacement. The shuttle/suicide plasmid was derived from the *E. coli* cloning vector, pGEM-3Zf(+), and the Gram-positive plasmid, pTV32, which contains the naturally thermosensitive replicon from pE194 (FIG. 2). The ≈6.4 kb BamH1 fragment of pTV32, containing the Ts replicon and a chloramphenicol resistance marker (cat), was ligated into the BamH1 site of pGEM-3Zf(+). The smaller PstI fragment of the resulting construct was dropped out and the larger fragment religated. pKM10 can be maintained in *B. cereus* at 28° C. and cured at 41° C.

The EcoRI fragment from pUC18 containing the mutant allele, hblA1, was subcloned into the unique EcoRI site of pKM10, and transformed into *E. coli*. The recombinant plasmid was confirmed by restriction digest analysis. pKM10::hblA1 was introduced into *B. cereus* AS4–12 by electroporation. Restriction digest analysis of plasmid DNA isolated from $Cm^r$ transformants verified the presence of the recombinant plasmid.

Gene replacement. Selection for plasmid integrants. AS4–12 containing pKM10::hblA1 was grown overnight at the permissive temperature (28° C.) in 50% TSB containing chloramphenicol to achieve a large population of plasmid-carrying cells. This culture was diluted 1:100 into nonselective broth and grown at 28° C. with shaking for two hours and then shifted to the nonpermissive temperature (41° C.) for 4–6 hours to eliminate or reduce the copy number of freely-replicating plasmid. The culture was plated at 41° C. on media containing chloramphenicol to select for cells in which the plasmid had integrated into the chromosome via a single crossover event between homologous regions of the wild-type and mutant hblA genes. The integration frequency was calculated as the ratio of colonies on selective plates to colonies on nonselective plates. PCR analysis with hblA primers served as an initial screen for the presence of the integrated plasmid, which was confirmed by Southern hybridization analysis of genomic DNA, probing with hblA.

Screen for second crossover event. A culture of the plasmid integrant was grown overnight at the restrictive temperature with chloramphenicol to obtain a large population of the integrant. The culture was diluted 100-fold into fresh broth and grown at 40° C. for 11 hr with or without Cm selection to allow for a second recombinational event to occur between the wild-type and mutant hblA genes. To cure any freely-replicating plasmid that had excised from the chromosome, the culture was diluted 1:100 into selective or nonselective broth and grown overnight (~12 hours) at 40° C. The outgrowth from the overnight culture was plated at 28° C. on nonselective media. Individual colonies were screened for loss of chloramphenicol resistance by patching onto TSA±Cm. The frequency of the second crossover event was calculated as the ratio of $Cm^s$ colonies to the total number of colonies screened. PCR and Southern blot analyses were performed to distinguish which of the $Cm^s$ colonies had replaced the wild-type gene with the mutant allele.

A first mutant clone ultimately selected for Western analysis and the hemolysis assay resulted from a culture that was subjected to selection until plating. To summarize, the mutant derivative of AS4–12, considered by the inventors to be a preferred embodiment of the invention, was constructed by a two-step gene replacement. In the first step, clones in which the plasmid had integrated into the chromosome via homologous recombination between hblA1 and $hblA^+$ were selected following growth at the nonpermissive temperature. In the second step, the plasmid integrant was screened for loss of chloramphenicol-resistance, resulting from a second crossover event and plasmid curing. The $Cm^s$ isolates were analyzed by PCR and Southern blot analysis to identify those which had undergone a successful gene replacement.

A second mutant has been identified. The mutant is characterized as having a deletion in hblA that corresponds to nucleotides 460–823 of the published hblA sequence (Heinrich, 1993). The second mutant was obtained using a process similar to that described in connection with the first mutant except that when the screen for the second crossover event was performed, the integrant was permitted to grow at 28° C. for several hours after establishing the large population of the integrant, because there is some evidence that growth at a permissive temperature can stimulate recombination between duplicate regions flanking an integrated plasmid in *Bacillus subtilis* and *Lactococcus lactis* (Noirot et al., 1987; Biswas et al., 1993). It is anticipated that the second mutant will be HBL enterotoxin-deficient.

Hemolysis assay. Culture supernatants of AS4–12 and the hblA mutants, prepared as described for Western blot analysis, were examined for the discontinuous pattern of hemolysis in a gel diffusion assay essentially as described previously (Beecher and Wong, 1994). Ten $\mu$l of culture supernatant were placed in a 4-mm-diameter well in HBL blood agar. The plates were incubated at room temperature, 28° C. or 37° C., and monitored periodically for hemolysis.

Complementation of hemolysis by $hblA^+$ in trans. An $hlbA^+$expression vector, pADhblA, derived from pAD123 (43–25) was constructed for complementation analysis of the mutants. This is not a true test of complementation because the hblA mutants are not $Rec^-$ strains, and therefore, $hblA^+$ could hypothetically recombine into the chromosome and re-form the wild-type genotype. Plasmid pAD123 (43–25) is an *E. coli*/*B. cereus* shuttle vector with an ampicillin resistance gene for selection in *B. coli*, a chloramphenicol resistance gene for selection in *B. cereus*, and a chromosomal insert from *B. cereus* UW85 cloned upstream from a promoterless gfp gene (Dunn and Handelsman, 1999). UW85 carrying pAD123(43–25) exhibits constitutive gfp expression during log-phase growth in BHIG. To construct the hblA expression vector, the gfp gene in pAD123(43–25) was removed and replaced with $hblA^+$. The XbaI-HindIII fragment containing gfp was removed from pAD123(43–25). The XbaI end of the plasmid was made blunt with Klenow fragment of DNA polymerase prior to digestion with HindIII. This fragment was ligated with the 1.7-kb SmaI-HindIII fragment from pUC18 containing $hblA^+$. Similar plasmids, containing either hblA1 (pADhblA1) or hblA2 (pADhblA2) were constructed as controls. The recombinant plasmids, verified by restriction digest analysis, were introduced into the appropriate *B. cereus* mutants. The resulting strains were assayed for the discontinuous pattern of hemolysis.

Vascular permeability (VP) assay. Beecher and Wong (1994) showed that HBL causes a vascular permeability response in rabbit skin, including necrosis at sufficient concentrations. An increase in vascular permeability allows leakage of serum proteins into the surrounding tissues. The reaction is quantitated by Evans blue dye, administered intravenously, which binds to the serum proteins, resulting in an area of bluing around the injection site. A strong reaction is characterized by an area of necrosis at the center of the zone of bluing. Culture supernatants were prepared and concentrated by ultrafiltration as described for Western blot analysis. The assay was performed essentially as described by Glatz et al. (1974). Briefly, 50-μl samples of culture supernatant were injected intradermally into the back of a shaved New Zealand White rabbit. Three hours after the injections, 1% Evans blue dye (1 ml/kg) was administered intravenously, and the diameters of bluing and necrosis were measured one hour later. Some rabbits were sedated with acepromazine (4 mg/kg) 10–30 min prior to the sample and dye injections.

For the neutralization experiments, 62.5 μl or 66.7 μl of 12×-concentrated culture supernatant was mixed with 30 μl of either preimmune, anti-B, or anti-$L_2$ rabbit serum, and then diluted with sterile distilled water to a supernatant concentration of 3× or 4×. The antisera were prepared against purified B or purified $L_2$ component from *B. cereus* F837/76 (Beecher et al., 1995).

Biocontrol assay. The biocontrol activity of AS4–12 and the mutants was examined in a growth-chamber tomato emergence assay (Smith et al., 1997). Bacterial strains were tested for the ability to suppress damping-off of tomato seedlings caused by *Pythium torulosum*. Inserts of a 72-cell bedding plant container that had been filled with autoclaved vermiculite (medium vermiculite premium grade, Strong-Lite Horticultural Products, Seneca, Ill.) were planted with seeds, 10 per cell, of tomato cultivar Wis. 55. A layer of vermiculite was added to cover the seeds. Four liters of deionized water either inoculated with 4 zoospores per seed or uninoculated were added to each planting tray flat. One ml of diluted bacterial culture that had been grown in 50% TSB for four days at 28° C. was distributed over ten seeds. The planting trays received supplemental water every 12 hr to maintain a constant level throughout the experiment. The assay was conducted at 24° C., 40% relative humidity, and with a 12-hour photoperiod. Emergence was scored twelve days after planting.

Cultures of the *B. cereus* strains diluted 1:2, 1:8, and 1:16 (culture: sterile MilliQ water), and untreated seeds were evaluated at pathogen doses of 0 and 4 zoospores per seed. The treatments were arranged in a randomized split plot design where the *P. torulosum* dose (0 or 4 zoospores per seed) comprised the main plots and the bacterial doses comprised the subplots. Each treatment consisted of 3 cells per plot, for a total of 30 seeds. Plots that received water only were replicated three times, while the plots that were inoculated with the pathogen were replicated five times to accommodate greater variability. The experiment was run two times. Fraction emergence was transformed by arcsine square-root before analysis. Mean emergence data from the two experiments was combined and analyzed by analysis of variance (Minitab release 10xtra, Minitab, Inc., State College, Pa.). ANOVA was conducted on each culture dilution and untreated control. Mean separation tests were performed according to Fisher's protected LSD (Snedecor and Cochran, 1980).

Results

Western immunoblot analysis. To determine whether mutants 41a and 10e2 secreted detectable quantities of the B component of HBL, immunoblot analysis was performed on culture supernatants with polyclonal antiserum to the B protein. Culture supernatant of AS4–12 contained at least two proteins that reacted with the antiserum, indicated by a strong ~37-kDa band that migrated to approximately the same position as purified B protein (37.8 kDa) isolated from *B. cereus* F837/76, and a weaker ~39-kDa band. Sequence heterogeneity between the hblA genes from F837/76 and AS4–12 likely accounts for the slight difference in mobility exhibited between the B component purified from F837/76 and that expressed from AS4–12. Culture supernatants of both mutants exhibited the 39-kDa band, and a faint ~37 kDa band. It is likely that this 37-kDa band is also present in AS4–12, and that its presence has been unmasked in the hblA mutants. This band may correspond to another protein that is antigenically related to the B component, or it may represent a proteolytic degradation product of the 39-kDa protein. Strains 41a$^+$ and 10e2$^+$, carrying the F837/76 hblA$^+$ gene in trans, accumulated the 37.8-kDa B component and the 39-kDa protein. Blots probed with preimmune rabbit serum did not display any reaction. The results suggest that mutants 41a and 10e2 do not accumulate the B component of HBL in culture supernatant, but that they may express, in addition to the 39-kDa protein, another protein that is immunologically related to the B component.

Hemolytic activity of mutants. Strains 41a and 10e2 were tested for the discontinuous pattern of hemolysis characteristic of HBL, in which lysis of erythrocytes in blood agar typically begins several millimeters away from a colony or well containing culture supernatant, resulting in a ring pattern (Beecher and Macmillan, 1990). Neither mutant exhibited the discontinuous hemolysis displayed by AS4–12, either around colonies or wells filled with concentrated culture supernatant. Introduction of hblA$^+$ in trans on a low-copy plasmid, pADhblA, restored the wild-type phenotype to both mutants. The results indicate that deletions of 123 or 364 bases in hblA abolishes activity by AS4–12 in the discontinuous hemolysis assay.

Vascular permeability assay. The toxicity of mutants 41a and 10e2 was compared to that of AS4–12 in the vascular permeability (VP) assay. Culture supernatants from both mutant strains produced reactions similar to AS4–12 at several doses. Unconcentrated supernatant from all three strains produced bluing, but no obvious necrosis, a result observed in several independent experiments. All three strains exhibited necrosis with 3x- and 6x-concentrated supernatants. Six-fold-concentrated BHIG culture medium did not cause a VP response.

To determine whether an alternative B protein(s) contributed to the VP activities displayed by the mutants, culture supernatant treated with antiserum to the B component was tested. Neutralization with anti-B serum did not attenuate the reactions caused by AS4–12 or 41a. However, it did appear to diminish the severity of the response elicited by mutant 10e2; i.e., the necrosis was eliminated, although the size of the bluing zone increased. In a second experiment, antiserum to B decreased the bluing caused by 10e2, and the necrosis caused by AS4–12. While these results are not conclusive, they suggest that a protein(s) that is antigenically related to the B component contributes to the VP activity in AS4–12 and the mutants. The contradictory results obtained with AS4–12, and the failure to detect any effect of anti-B serum on the VP activity elicited by mutant 41a, may indicate that a threshold level of neutralization is necessary to cause a detectable reduction in the VP response.

Neutralization with antiserum to the $L_2$ component appeared to reduce both the bluing and necrosis caused by all three strains, indicating that the $L_2$ component and/or an alternate $L_2$ protein contributes to the VP activity in AS4–12 and both hblA mutants. This result indirectly implicates the participation of a B-like protein in the VP activity exhibited by the hblA mutants, as Beecher and Wong (1994) found that the combination of purified $L_1$ and $L_2$ components failed to cause any dermal reaction in the VP assay.

Biocontrol ability of hblA mutants. Mutants 41a and 10e2 were tested for their ability to suppress damping-off of tomato seedlings caused by *P. torulosum* in a growth chamber assay. Tomato seeds were coinoculated with zoospores of the pathogen and sporulated cultures of AS4–12, 41a, or 10e2. Culture dilutions of 1:2, 1:8 and 1:16 were tested for biocontrol ability. All three strains significantly increased seedling emergence compared to the untreated control ($\alpha$=0.05), and neither mutant differed significantly from the parental strain at any of the bacterial doses ($\alpha$=0.05). In the absence of pathogen, none of the bacterial treatments influenced emergence compared to the untreated control (data not shown). These results suggest that the B component of HBL does not contribute to biocontrol by AS4–12 in the lab.

Grain yield. Preliminary field data support the growth chamber assay results. AS4–12 and 41a were evaluated for soybean yield-enhancing ability at two sites in Wis. during the 1998 field season (Oplinger et al., unpublished data). Soybean seeds coated with 41a and AS 4–12 exhibited a significant increase in yield over untreated seeds at both sites (P=0.001). AS 4–12 and 41a increased soybean yield by 6.2% and 8.0%, respectively, at one site, and by 8.8% and 14.7% at a second site. Preliminary analysis suggests that the difference between the AS 4–12 and 41a treatments at the second site was significant (LSD=10%). The superior performance of the hblA mutant at this site may be an anomalous result, although removal of this gene could might actually enhance biocontrol ability. Alternatively, another genetic difference between 41a and the parent strain could account for the yield difference.

CITATIONS

All of the following citations are incorporated herein by reference in their entirety.

Agata, N., Ohta, M., Yoshichika, A., and Mori, M. 1995. The bceT gene of *Bacillus cereus* encodes an enterotoxic protein. Microbiology 141:983–988.

Ash, C., Farrow, J. A. E., Dorsch, M., Stackebrandt, E. & Collins, M. D. 1991a. Comparative analysis of *Bacillus anthracis, Bacillus cereus*, and related species on the basis of reverse transcriptase sequencing of 16S rRNA. Int. J. Syst. Bacteriol. 41:343–346.

Ash, C., Farrow, J. A. E., Wallbanks, S. & Collins, M. D. 1991b. Phylogenetic heterogeneity of the genus Bacillus revealed by comparative analysis of small-subunit-ribosomal RNA sequences. Letters in Appl. Microbiol. 13:202–206.

Beecher, D. J., and Macmillan, J. D., 1991. Characterization of the components of hemolysin BL from *Bacillus cereus*. Infect. Immun. 59: 1778–1784.

Beecher, D. J., J. L. Schoeni and A. C. L. Wong. 1995. Enterotoxic activity of hemolysin BL from *Bacillus cereus*. Infect. Immun. 63:4423–4428.

Beecher, D. J. and A. C. L. Wong. 1994. Identification of hemolysin BL-producing *Bacillus cereus* isolates by a discontinuous hemolytic pattern on blood agar. Appl. Environ. Microbiol. 60:1646–1651.

Benbrook, C. M., Groth, E., Halloran, J. M., Hansen, M. K., Marquardt, S. 1996. Pest Management at the Crossroads. Consumers Union, Yonkers, N.Y.

Biswas, I., Gruss, A., Ehrlich, S. D., and Maguin, E. (1993). High-efficiency gene inactivation and replacement system for gram-positive bacteria. J. Bact. 175: 3628–3635.

Carlson, C. R., Caugant, D. A. & Kolsto, A.-B. 1994. Genotypic diversity among *Bacillus cereus* and *Bacillus thuringiensis* strains. Appl. Environ. Microbiol. 60:1719–1725.

Cook, R. J., Bruckart, W. L., Coulson, J. R., Goettel, M. S., Humber, R. A., Lumsden, R. D., Maddox, J. V., McManus, M. L., Moore, L., Meyer, S. F., Quimby, P. C. Jr, Stack, J. P., Vaughn, J. L. 1996. Safety of Microorganisms Intended for Pest and Plant Disease Control: A Framework for Scientific Evaluation. Biol. Control 7:333–351.

Damgaard, P. H. 1995. Diarrhoeal enterotoxin production by strains of *Bacillus thuringiensis* isolated from commercial *Bacillus thuringiensis*-based insecticides. FEMS Immunol. Med. Microbiol. 12:245–249.

Damgaard, P. H, Larsen, H. D., Hansen, B. M., Bresciani, J. and Jorgensen, K. (1996). Enterotoxin-producing strains of *Bacillus thuringiensis* isolated from food. Lett. Appl. Microbiol. 23: 146–150.

Dunn, A. K. and J. Handelsman. 1999. A vector for promoter trapping in *Bacillus cereus*. Gene 226:297–305 (1999).

Gilbert, R. J. (1979). In *Food-borne infections and intoxications*, 2nd ed., pp. 495–518. Edited by H. Rieman and F. L. Bryan. Academic Press, New York.

Gilbert, G. S., Parke, J. L., Clayton, M. K., and Handelsman, J. 1993. Effects of an introduced bacterium on bacterial communities on roots. Ecology 74:840–854.

Glatz, B. A., Spira, W. M., and Goepfert, J. M. 1974. Alteration of vascular permeability in rabbits by culture filtrates of *Bacillus cereus* and related species. Infect. Immun. 10:299–303.

Gordon, R. E. 1975. Some taxonomic observations on the genus Bacillus. In *Biological Regulation of Vectors: The saprophytic and aerobic bacteria and fungi*, pp. 67–82. Edited by J. D. Briggs. Easton, MD: U. S. Dept. of Health and Human Services.

Govan, J. R. W., and Deretic, V. 1996. Microbial pathogenesis in cystic fibrosis: mucoid *Pseudomonas aeruginosa* and *Burkholderia cepacia*. Microbiol. Rev. 60:539–574.

Granum, P. E., Brynestad, S., and Kramer, J. M. 1993. Analysis of enterotoxin production by *Bacillus cereus* from dairy products, food poisoning incidents and non-gastrointestinal infections. Int. J. Food Microbiol. 17: 269–279.

Halverson, L. J., Clayton, M. K., and Handelsman, J. 1993. Population biology of *Bacillus cereus* UW85 in the rhizosphere of field-grown soybeans. Soil Biol. Biochem. 25:485–493.

Handelsman, J., Raffel, S. J., Mester, E. H., Wunderlich, L. and Grau, C. R. 1990. Biological control of damping-off of alfalfa seedlings by *Bacillus cereus* UW85. Appl. Environ. Microbiol. 56:713–718.

He, H., Silo-Suh, L. A., Handelsman, J., and Clardy, J. 1994. Zwittermicin A, an antifungal and plant protection agent from *Bacillus cereus*. Tetrahedron Letters 35:2499–2502.

Heinrichs, J. H., Beecher, D. J., Macmillan, J. D., and Zilinskas, B. A. (1993). Molecular cloning and characterization of the hblA gene encoding the B component of hemolysin BL from *Bacillus cereus*. J. Bact. 175: 6760–6766.

Kim, D.-S., Weller, D. M., Cook, R. J. (1997). Populations dynamics of Bacillus sp. L324–92$R_{12}$ and *Pseudomonas fluorescens* 2–79$RN_{10}$ in the rhizosphere of wheat. Phytopathology 87:559–564.

Laemmli, U. K. 1970. Cleavage of structural proteins during the assembly of the head of bacteriophage T4. Nature 227:680–685.

Lee, P. K., Buswell, J. A., and Shinagawa, K. (1995). Technical Report: Distribution of toxigenic *Bacillus cereus* in rice samples marketed in Hong Kong. World Journal of Microbiology & Biotechnology 11: 696–698.

Logan, N. A. & Berkeley, R. C. W. 1984. Identification of Bacillus strains using the API system. J. Gen. Microbiol. 130:1871–1882.

Lysenko, O. 1983. *Bacillus thuringiensis*: evolution of taxonomic concept. J. Invertebr. Pathol. 42:295–298.

Macaluso, A. and Mettus, A.-M. (1991). Efficient transformation of *Bacillus thuringiensis* requires nonmethylated plasmid DNA. J. Bact. 173:1353–1356.

Milner, J. L., Stohl, E. A., and Handelsman, J. (1996). Zwittermicin A resistance gene from *Bacillus cereus*. J. Bact. 178: 4266–4272.

Mosso, A., Arribas, L. G., Cuena, J. A., and de la Rosa, C. (1989). Enumeration of Bacillus and *Bacillus cereus* Spores in Food from Spain. J. Food Protection 52: 184–188.

Noirot, Ph., Petit, M. A., and Ehrlich, S. D. (1987). Plasmid replication stimulates DNA recombination in *Bacillus subtilis*. J. Mol. Biol. 196: 39–48.

Osburn, R. M., Milner, J. L., Oplinger, E. S., Smith, R. S., and Handelsman, J. 1995. Effect of *Bacillus cereus* UW85 on the yield of soybean at two field sites in Wis. Plant Dis. 79:551–556.

Parke, J. L., Rand, R. E., and Joy, A. E. 1991. Biological control of Pythium damping-off and Aphanomyces root rot of peas by application of *Pseudomonas cepacia* or *P. fluorescens* to seed. Plant Dis. 75:987–992.

Priest, F. G. 1993. Systematics and ecology of Bacillus. In *Bacillus subtilis* and *Other Gram-Positive Bacteria*, pp. 9–10. Edited by A. L. Sonenshein, J. A. Hoch & R. Losick. Wash., D. C.: American Society for Microbiology.

Raffel, S. J., Stabb, E. V., Milner, J. L., and Handelsman, J. (1996). Genotypic and phenotypic analysis of zwittermicin A-producing strains of *Bacillus cereus*. Microbiol. 42: 3425–3436.

Ryan, P. A., MacMillan, J. D., and Zilinskas, B. A.1997. Molecular cloning and characterization of the genes encoding the $L_1$ and $L_2$ components of hemolysin BL from *Bacillus cereus*. J. Bacteriol. 179: 2551–2556.

Stabb, E. V., Jacobson, L. M., and Handelsman, J. (1994). Zwittermicin A-producing strains of *Bacillus cereus* from diverse soils. Appl. Environ. Microbiol. 60: 4404–4412.

Sambrook, J., Fritsch, E. F., and Maniatis, T. (1989). Molecular cloning: a laboratory manual, 2nd ed. Cold Spring Harbor Laboratory Press, Cold Spring Harbor, N.Y.

Silo-Suh, L. A., Lethbridge, B., Raffel, S., He, H., Clardy, J. and Handelsman, J. (1994). Biological activities of two fungistatic antibiotics produced by *Bacillus cereus* UW85. Appl. Environ. Microbiol. 60: 2023–2030.

Smith, K. P., J. Handelsman and R. M. Goodman. 1997. Modeling of dose-response relationships in biological control: partitioning host response to the pathogen and biocontrol agent. Biol. Control 87:720–729.

Snedecor, G. W. and W. G. Cochran. 1980. Statistical methods, 7th ed. The Iowa State University Press, Ames, Iowa.

Te Giffel, M. C., Beumer, R. R., Granum, P. E., and Rombouts, F. M. (1997). Isolation and characterization of *Bacillus cereus* from pasteurized milk in household refrigerators in the Netherlands. Int. J. Food Microbiol. 34: 307–318.

Yusuf, I. Z., Umoh, V. J., and Ahmad, A. A. (1992). Occurrence and survival of enterotoxigenic *Bacillus cereus* in some Nigerian flour-based foods. Food Control 3: 149–153.

Zahner, V., Momen, H., Salles, C. A. & Rabinovitch, L. 1989. A comparative study of enzyme variation in *Bacillus cereus* and *Bacillus thuringiensis*. J. Appl. Bacteriol. 67:275–282.

We claim:

1. A method for obtaining a mutant Bacillus, the method comprising the steps of:
   mutating a Bacillus to introduce a mutation in hblA that prevents formation of an active Niemolysin BL enterotoxin; and
   selecting a mutant Bacillus comprising the mutation,
   wherein the Bacillus is selected from the group consisting of B. cereus, B. thuringiensis and B. anthracis.

2. A method as claimed in claim 1 wherein the introduced mutation is selected from the group consisting of a point mutation, a deletion, an insertion, and a rearrangement.

3. A method as claimed in claim 1 wherein the mutation is a deletion.

4. A method as claimed in claim 1 wherein the Bacillus and the mutant Bacillus suppress damping-off of tomato seedlings caused by Pythium torulosum in a growth chamber assay.

5. A method as claimed in claim 4 wherein the Bacillus produces zwittermicin A.

6. A method as claimed in claim 4, wherein the Bacillus is a Bacillus cereus selected from the group consisting of UW85, AS4-12, MS1-9 and DGA34.

7. A method for obtaining a mutant Bacillus cereus AS4–12, the method comprising the steps of:
   mutating strain AS4–12 to introduce a mutation in hblA that prevents formation of an active Hemolysin BL enterotoxin; and
   selecting a mutant of strain AS–12 that comprises the mutation.

8. A method as claimed in claim 7 wherein the mutant comprises a deletion in hblA relative to Bacillus cereus strain AS4 –12.

9. A Bacillus having a mutation in hblA that prevents formation of an active Hemolysin BL enterotoxin, wherein the Bacillus supresses damping-off of tomato seedlings caused by Pythium torulosum in a growth chamber assay and is selected from the group consisting of B. cereus, B. thuringiensis and B. anthracis.

10. A Bacillus cereus as claimed in claim 9 wherein the Bacillus cereus produces zwittermicin A.

11. A Bacillus cereus as claimed in claim 9 selected from the group consisting of a mutant of UW85, a mutant of AS4–12, a mutant of MS1–9 and a mutant of DGA34.

12. A Bacillus cereus as claimed in claim 11 wherein the Bacillus cereus is a mutant of AS4–12 having a deletion in hblA relative to strain AS4–12.

13. A Bacillus cereus as claimed in claim 12 wherein the deleted hblA has a sequence of SEQ ID NO: 1.

14. A Bacillus cereus as claimed in claim 12 wherein the deleted hblA has a sequence of FIG. 2 with nucleotides 460 to 823 deleted.

* * * * *

UNITED STATES PATENT AND TRADEMARK OFFICE
CERTIFICATE OF CORRECTION

PATENT NO.     : 6,602,712 B2                                      Page 1 of 1
DATED          : August 5, 2003
INVENTOR(S)    : Jo Handelsman and Amy K. Klimowicz It is certified that error appears in the above-identified patent and that said Letters Patent is hereby corrected as shown below:

<u>Column 1,</u>
Line 7, please delete the entire paragraph and insert therefor the following:

-- This invention was made with United States government support awarded by the following agencies:

DOE Grant No.: DE-FG02-96ER20248
    NIH Grant No.: RR02301
    USDA Hatch # 3676 & 4038; 94-37313-0676
    USDA Grant No.: IR4 94-34108-0002; 58-3148-6-029

The Unites States has certain rights in this invention. --

<u>Column 21,</u>
Line 41, please delete the word "Niemolysin" and insert therefor -- Hemolysin --.

Signed and Sealed this

Twenty-fifth Day of November, 2003

JAMES E. ROGAN
*Director of the United States Patent and Trademark Office*